(12) United States Patent
Hientzsch et al.

(10) Patent No.: US 9,895,177 B2
(45) Date of Patent: Feb. 20, 2018

(54) BONE FIXATION DEVICE FOR TREATMENT OF FEMORAL FRACTURES

(71) Applicant: ARTHREX GMBH, Munich (DE)

(72) Inventors: Marcus Hientzsch, Munich (DE); Gerlinde Michel, Munich (DE); Georg Gradl, Baldham (DE)

(73) Assignee: ARTHREX, GmbH (DE)

( * ) Notice: Subject to any disclaimer, the term of this patent is extended or adjusted under 35 U.S.C. 154(b) by 0 days.

(21) Appl. No.: 15/054,472

(22) Filed: Feb. 26, 2016

(65) Prior Publication Data

US 2017/0202584 A1 Jul. 20, 2017

Related U.S. Application Data

(60) Provisional application No. 62/279,161, filed on Jan. 15, 2016.

(51) Int. Cl.
| | | |
|---|---|---|
| A61B 17/34 | (2006.01) |
| A61B 17/72 | (2006.01) |
| A61B 17/74 | (2006.01) |
| A61B 17/86 | (2006.01) |
| A61B 17/16 | (2006.01) |

(52) U.S. Cl.
CPC .......... *A61B 17/72* (2013.01); *A61B 17/3472* (2013.01); *A61B 17/744* (2013.01); *A61B 17/8645* (2013.01); *A61B 17/164* (2013.01); *A61B 17/1659* (2013.01); *A61B 17/7241* (2013.01)

(58) Field of Classification Search
CPC . A61B 17/8685; A61B 17/725; A61B 17/683; A61B 17/744; A61B 17/746; A61B 17/7241; A61B 17/72; A61B 17/742; A61B 17/7233; A61B 17/7266; A61B 17/3472; A61B 17/8645; A61B 2017/681; A61B 2017/00526
USPC ...................................... 606/62–67; 600/207
See application file for complete search history.

(56) References Cited

U.S. PATENT DOCUMENTS

| 722,105 A | 3/1903 | Hervey |
| 5,032,125 A * | 7/1991 | Durham ............... A61B 17/744 606/309 |
| 5,454,813 A | 10/1995 | Lawes et al. |

(Continued)

FOREIGN PATENT DOCUMENTS

| EP | 969774 B1 | 5/2003 |
| EP | 968685 B1 | 9/2004 |

(Continued)

OTHER PUBLICATIONS

US 9,179,949, 11/2015, Haidukewych et al. (withdrawn)

*Primary Examiner* — Pedro Philogene
(74) *Attorney, Agent, or Firm* — Carlson, Gaskey & Olds, P.C.

(57) ABSTRACT

A bone fixation device according to an exemplary aspect of the present disclosure includes a nail extending along a longitudinal axis. The nail is provided with a transverse bore arranged along a transverse axis that intersects the longitudinal axis. The bone fixation device further includes a screw assembly received in the transverse bore, and a locking device. The locking device is configured to clasp the screw assembly to lock the screw assembly against movement along the transverse axis and against rotation about the transverse axis.

25 Claims, 11 Drawing Sheets

(56) References Cited

U.S. PATENT DOCUMENTS

| | | | |
|---|---|---|---|
| 5,490,852 A | 2/1996 | Azer | |
| 5,707,374 A | 1/1998 | Schmidt et al. | |
| 6,143,012 A | 11/2000 | Gausepohl et al. | |
| 6,221,074 B1 | 4/2001 | Cole et al. | |
| 6,228,086 B1 | 5/2001 | Wahl et al. | |
| 6,235,031 B1 * | 5/2001 | Hodgeman | A61B 17/744 606/64 |
| 6,402,753 B1 | 6/2002 | Cole et al. | |
| 6,406,477 B1 | 6/2002 | Fujiwara | |
| 6,443,954 B1 | 9/2002 | Bramlet et al. | |
| 6,558,388 B1 | 5/2003 | Bartsch et al. | |
| 6,569,165 B2 | 5/2003 | Wahl et al. | |
| 6,648,889 B2 * | 11/2003 | Bramlet | A61B 17/744 606/310 |
| 6,932,819 B2 | 8/2005 | Wahl et al. | |
| 7,018,380 B2 | 3/2006 | Cole | |
| 7,041,104 B1 | 5/2006 | Cole et al. | |
| 7,182,765 B2 | 2/2007 | Roth et al. | |
| 7,232,442 B2 | 6/2007 | Sohngen et al. | |
| 7,306,600 B2 | 12/2007 | Roth et al. | |
| 7,527,627 B2 | 5/2009 | Ferrante et al. | |
| 7,534,244 B2 | 5/2009 | Ferrante et al. | |
| 7,591,819 B2 | 9/2009 | Zander et al. | |
| 7,670,340 B2 | 3/2010 | Brivio et al. | |
| 7,763,022 B2 | 7/2010 | Speitling et al. | |
| 7,780,667 B2 | 8/2010 | Watanabe et al. | |
| 7,799,030 B2 | 9/2010 | Watanabe et al. | |
| 7,850,690 B2 | 12/2010 | Frigg et al. | |
| 7,867,231 B2 | 1/2011 | Cole | |
| 7,883,509 B2 | 2/2011 | Ferrante et al. | |
| 7,918,853 B2 | 4/2011 | Watanabe et al. | |
| 8,092,454 B2 | 1/2012 | Sohngen | |
| 8,100,911 B2 | 1/2012 | Yamazaki et al. | |
| 8,187,275 B2 | 5/2012 | Ferrante et al. | |
| 8,303,590 B2 | 11/2012 | Elghazaly et al. | |
| 8,454,606 B2 | 6/2013 | Frigg et al. | |
| 8,491,584 B1 | 7/2013 | Fagan | |
| 8,668,695 B2 | 3/2014 | Schwammberger et al. | |
| 8,702,707 B2 | 4/2014 | Sohngen | |
| 8,715,283 B2 | 5/2014 | Brumfield et al. | |
| 8,808,292 B2 | 8/2014 | Velikov | |
| 8,808,293 B2 * | 8/2014 | Buettler | A61B 17/8891 606/64 |
| 8,961,522 B2 | 2/2015 | Metzinger et al. | |
| 9,044,283 B2 | 6/2015 | Simon | |
| 9,072,552 B2 | 7/2015 | Simon et al. | |
| 9,433,448 B2 | 9/2016 | Ehmke et al. | |
| 9,433,451 B2 | 9/2016 | Ehmke et al. | |
| 2006/0155281 A1 * | 7/2006 | Kaup | A61B 17/7258 606/65 |
| 2008/0294164 A1 | 11/2008 | Frank et al. | |
| 2010/0179551 A1 | 7/2010 | Keller et al. | |
| 2010/0249781 A1 | 9/2010 | Haidukewych et al. | |
| 2012/0197255 A1 | 8/2012 | Elghazaly | |
| 2013/0041414 A1 * | 2/2013 | Epperly | A61B 17/7225 606/310 |
| 2013/0274745 A1 | 10/2013 | Kmiec, Jr. | |
| 2014/0058392 A1 | 2/2014 | Mueckter et al. | |
| 2014/0074093 A9 | 3/2014 | Nelson et al. | |
| 2014/0135767 A1 | 5/2014 | Schwammberger et al. | |
| 2015/0080893 A1 * | 3/2015 | Graca | A61B 17/1707 606/64 |
| 2015/0209090 A1 | 7/2015 | Simon et al. | |
| 2015/0320461 A1 | 11/2015 | Ehmke | |

FOREIGN PATENT DOCUMENTS

| | | |
|---|---|---|
| EP | 1199995 B1 | 9/2007 |
| EP | 1558159 B1 | 11/2007 |
| EP | 1663036 B1 | 11/2009 |

* cited by examiner

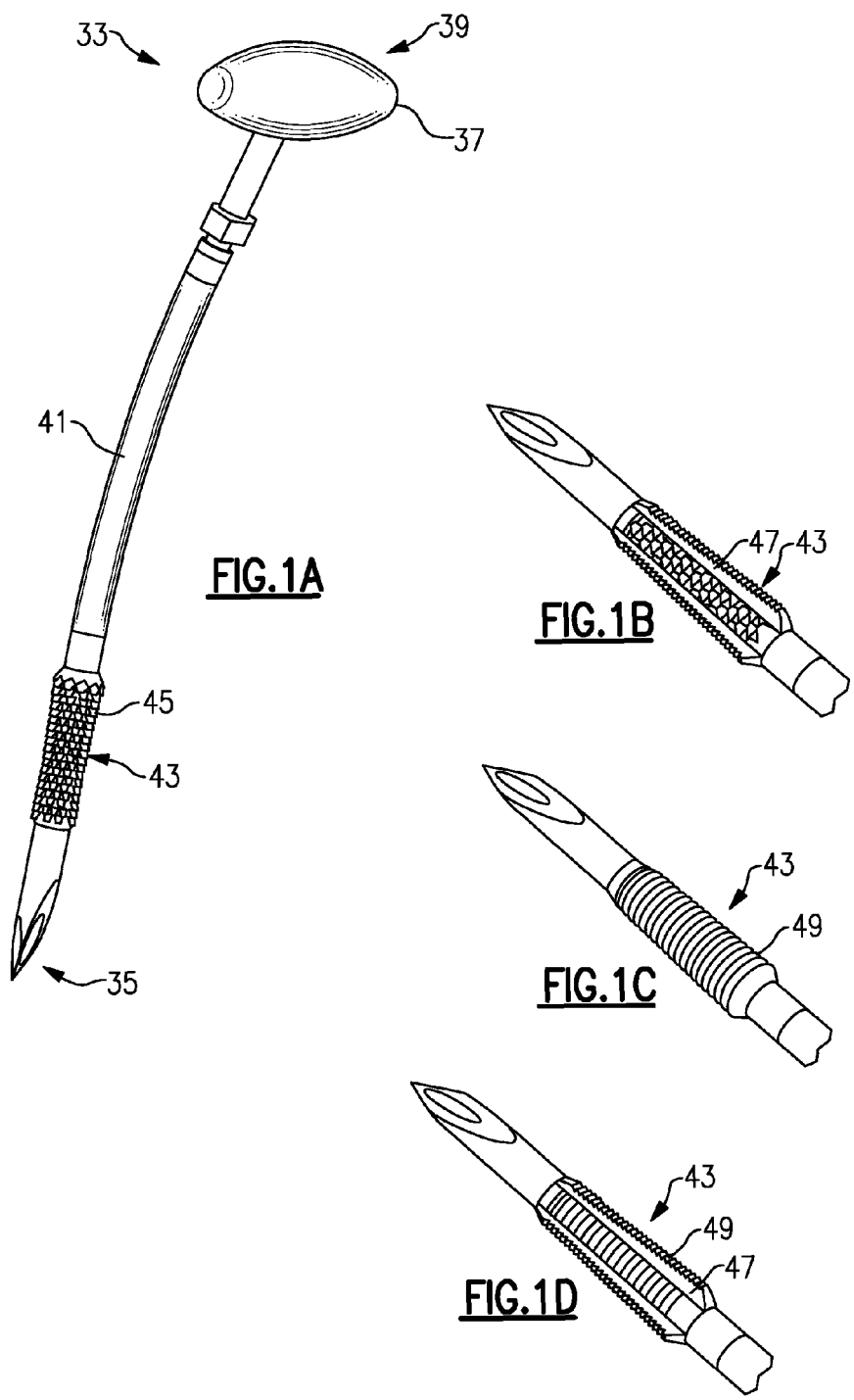

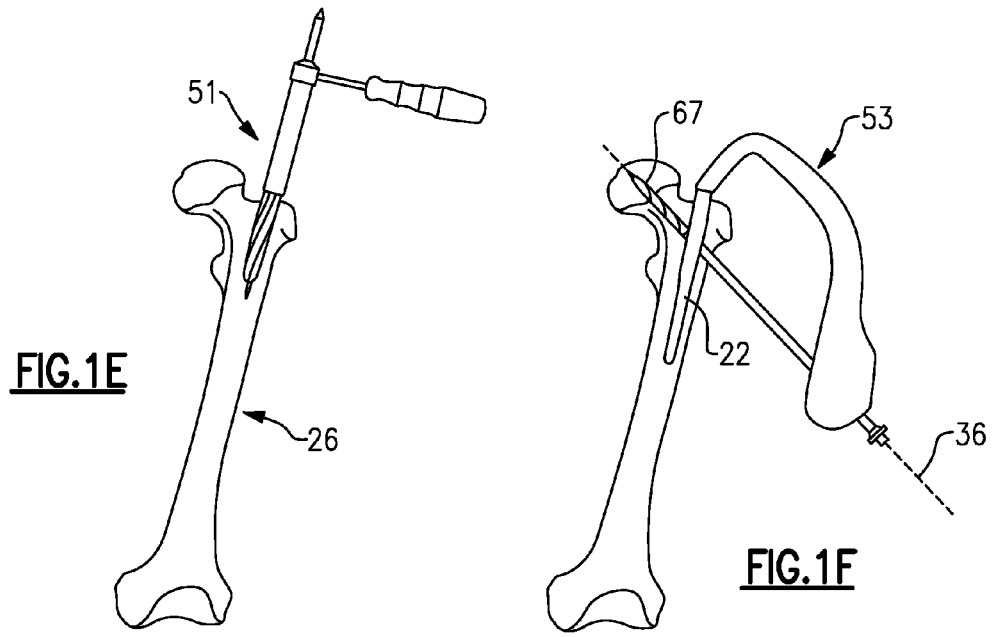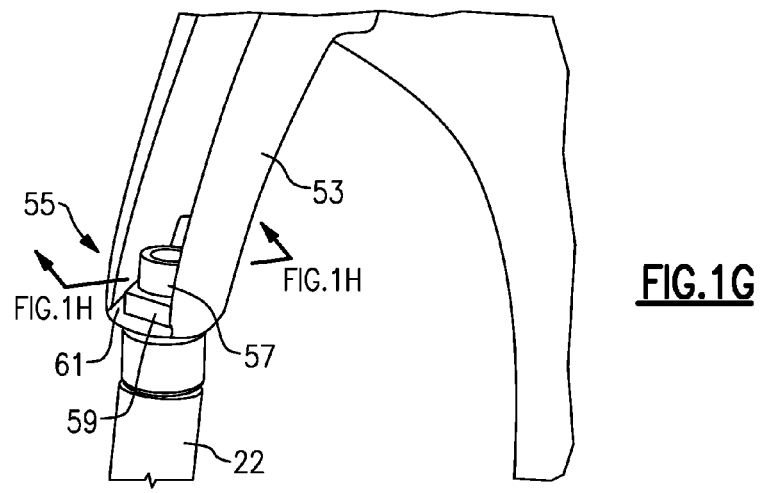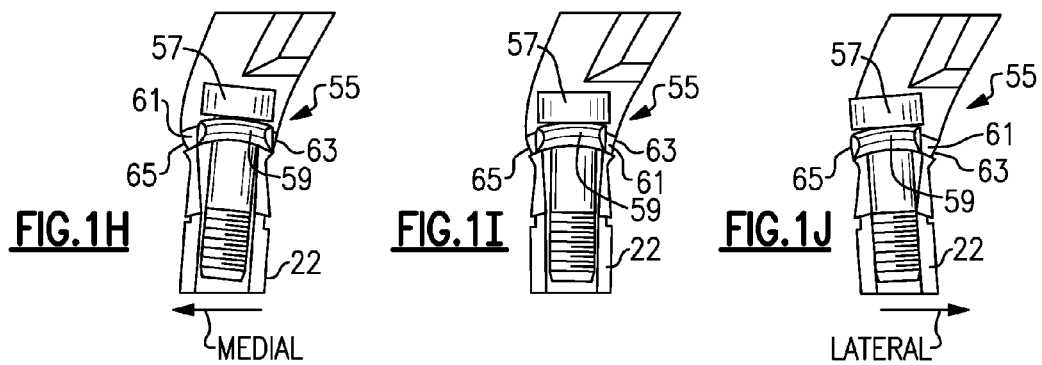

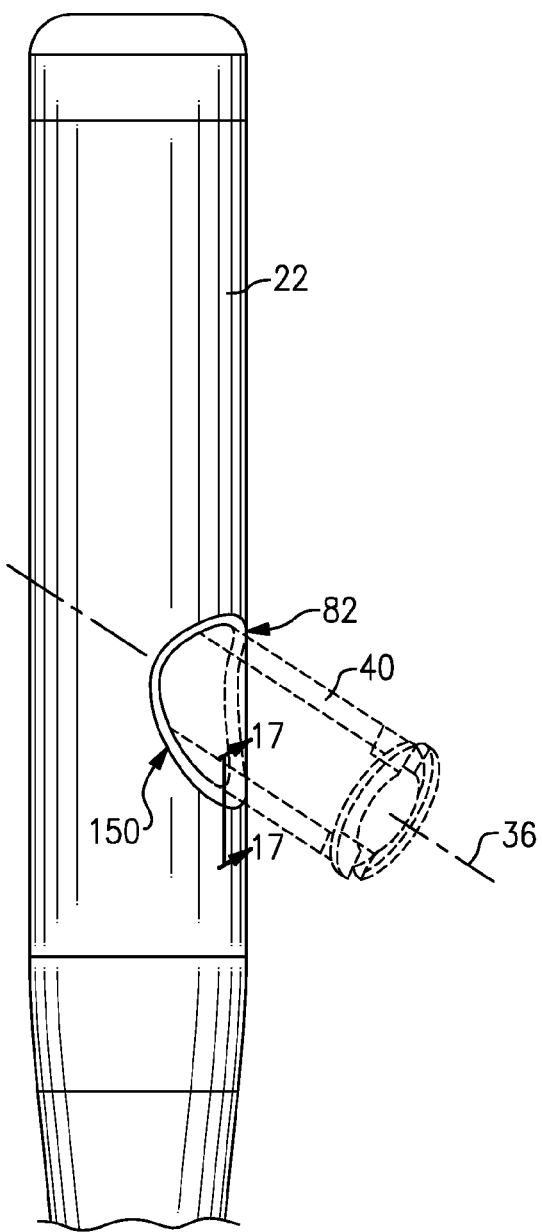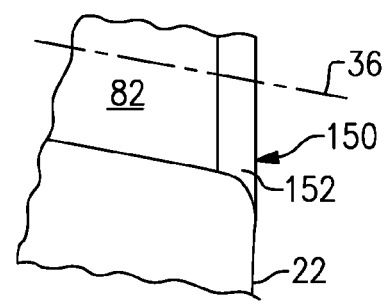
FIG.17
FIG.16

LATERAL  MEDIAL

LATERAL  MEDIAL

BONE FIXATION DEVICE FOR TREATMENT OF FEMORAL FRACTURES

RELATED APPLICATIONS

This application claims the benefit of U.S. Provisional Application No. 62/279,161, filed Jan. 15, 2016, the entirety of which is herein incorporated by reference.

BACKGROUND

This disclosure is related to a bone fixation device for treatment of a fracture, such as a femoral fracture.

Femoral nails are used to treat fractures of the femur by using one or more transverse screws to lock and stabilize a fractured portion of the femur, such as the femoral head or trochanter. The fracture may be caused by a traumatic injury or as the result of other medical conditions such as bone defects or tumors. Typically, a nail (sometimes called a "rod") is inserted into the medullary cavity of the femur. Once inserted, a screw is directed through a transverse bore and engages the femoral head. The screw is then locked relative to the nail, which in turn supports the femoral head relative to the remainder of the femur to promote healing of the bone.

SUMMARY

This disclosure relates to a bone fixation device including a nail and a transverse screw assembly. The transverse screw assembly is configured to maintain a position of a fractured bone fragment relative to the remainder of a bone. In one example, the fixation device is used to promote healing of a femoral fracture by stabilizing a femoral head.

A bone fixation device according to an exemplary aspect of the present disclosure includes a nail extending along a longitudinal axis. The nail is provided with a transverse bore arranged along a transverse axis that intersects the longitudinal axis. The bone fixation device further includes a screw assembly received in the transverse bore, and a locking device. The locking device is configured to clasp the screw assembly to lock the screw assembly against movement along the transverse axis and against rotation about the transverse axis.

In a further non-limiting embodiment of the foregoing bone fixation device, the screw assembly includes a sleeve provided with a first pattern. Further, a distal end of the locking device is provided with a second pattern configured to mate with the first pattern to lock the sleeve against movement along the transverse axis and against rotation about the transverse axis.

In a further non-limiting embodiment of any of the foregoing bone fixation devices, the first and second patterns are provided by one of (1) a wave-like knurled surface, (2) a diamond knurled surface, (3) a plurality of splines, (4) a recessed flat, and (5) a recessed ellipse-shape.

In a further non-limiting embodiment of any of the foregoing bone fixation devices, a lateral edge of the transverse bore is chamfered about its entire circumference.

In a further non-limiting embodiment of any of the foregoing bone fixation devices, a lateral edge of the transverse bore is rounded with tangential transitions about its entire circumference.

In a further non-limiting embodiment of any of the foregoing bone fixation devices, the screw assembly includes a sleeve and a screw, the screw is received in a bore of the sleeve, and the sleeve is configured to limit axial movement and restrict rotation of the screw about the transverse axis.

In a further non-limiting embodiment of any of the foregoing bone fixation devices, the screw includes an exterior surface with a channel, and a pin projects into the channel to restrict relative rotation of the screw about the transverse axis.

In a further non-limiting embodiment of any of the foregoing bone fixation devices, the sleeve includes a face configured to abut an outward projection of the screw.

In a further non-limiting embodiment of any of the foregoing bone fixation devices, the sleeve includes a face configured to abut a latch of the screw.

In a further non-limiting embodiment of any of the foregoing bone fixation devices, the screw assembly includes a screw having a distal end with threads and a rounded nose.

In a further non-limiting embodiment of any of the foregoing bone fixation devices, the distal end includes reverse threads.

In a further non-limiting embodiment of any of the foregoing bone fixation devices, the locking device is received in a bore in a proximal end of the nail, and the locking device is moveable along the longitudinal axis of the nail without rotating.

In a further non-limiting embodiment of any of the foregoing bone fixation devices, a set screw is received in the bore in the proximal end of the nail. Further, rotation of the set screw results in movement of the locking device along the longitudinal axis of the nail.

In a further non-limiting embodiment of any of the foregoing bone fixation devices, the bone fixation device is a proximal femoral nail.

A bone fixation device according to another exemplary aspect of the present disclosure includes, among other things, a nail extending along a longitudinal axis. The nail is provided with a transverse bore arranged along a transverse axis that intersects the longitudinal axis. The bone fixation device further includes a screw assembly received in the transverse bore. The screw assembly includes a sleeve provided with a first pattern. Additionally, the bone fixation device includes a locking device configured to clasp the screw assembly to lock the screw assembly against movement along the transverse axis and against rotation about the transverse axis. A distal end of the locking device is provided with a second pattern configured to mate with the first pattern to lock the sleeve against movement along the transverse axis and against rotation about the transverse axis.

In a further non-limiting embodiment of the foregoing bone fixation device, the sleeve is configured to limit axial movement and restrict rotation of the screw about the transverse axis.

In a further non-limiting embodiment of any of the foregoing bone fixation devices, the screw includes an exterior surface with a channel, and a pin projects into the channel.

A method of fixing fractured bone fragments relative to one another to promote healing according to an exemplary aspect of the present disclosure includes, among other things, inserting a nail into a medullary cavity of a bone. The nail extends along a longitudinal axis and a transverse bore arranged along a transverse axis that intersects the longitudinal axis. The method further includes engaging a fractured fragment of the bone with a screw received through the transverse bore, and positioning a sleeve provided outside the screw within the transverse bore. The sleeve is configured to limit movement of the screw along the transverse axis, and to prevent rotation of the screw about the transverse axis. Further still, the method includes clasping an exterior surface of the sleeve with a locking device. The locking device is configured to prevent movement of the sleeve along the transverse axis, and to prevent rotation of the sleeve about the transverse axis.

In a further non-limiting embodiment of the foregoing method, a pin projecting into a channel formed in an exterior surface of the screw. The pin limits the axial movement of the screw relative to the transverse axis and prevents rotation of the screw about the transverse axis.

In a further non-limiting embodiment of any of the foregoing methods, the step of positioning the sleeve includes positioning a femoral head to promote healing of the fractured fragment.

The embodiments, examples and alternatives of the preceding paragraphs, the claims, or the following description and drawings, including any of their various aspects or respective individual features, may be taken independently or in any combination. Features described in connection with one embodiment are applicable to all embodiments, unless such features are incompatible.

BRIEF DESCRIPTION OF THE DRAWINGS

The drawings can be briefly described as follows:

FIG. 1A illustrates an example cannulated awl with a first example rasper.

FIG. 1B illustrates a second example rasper.

FIG. 1C illustrates a third example rasper.

FIG. 1D illustrates a fourth example rasper.

FIG. 1E illustrates a reamer relative to a fractured bone.

FIG. 1F illustrates an aiming jig, nail, and another reamer relative to a fractured bone.

FIG. 1G is a partial view of an example aiming jig.

FIG. 1H is a cross-sectional view illustrating a first aiming jig orientation.

FIG. 1I is a cross-sectional view illustrating a second aiming jig orientation.

FIG. 1J is a cross-sectional view illustrating a third aiming jig orientation.

In FIG. 7, the screw assembly is received in a transverse bore of a nail, and is connected to the nail by way of a locking device.

FIG. 16 illustrates a rounded lateral edge of the transverse bore.

FIG. 17 is a view taken along line 17-17 and illustrates the rounded lateral edge in detail.

DETAILED DESCRIPTION

This disclosure relates to a bone fixation device including a nail and a transverse screw assembly. The transverse screw assembly is configured to maintain a position of a fractured bone fragment relative to the remainder of a bone. In one example, the fixation device is used to promote healing of a femoral fracture by stabilizing a femoral head.

Figure 1:
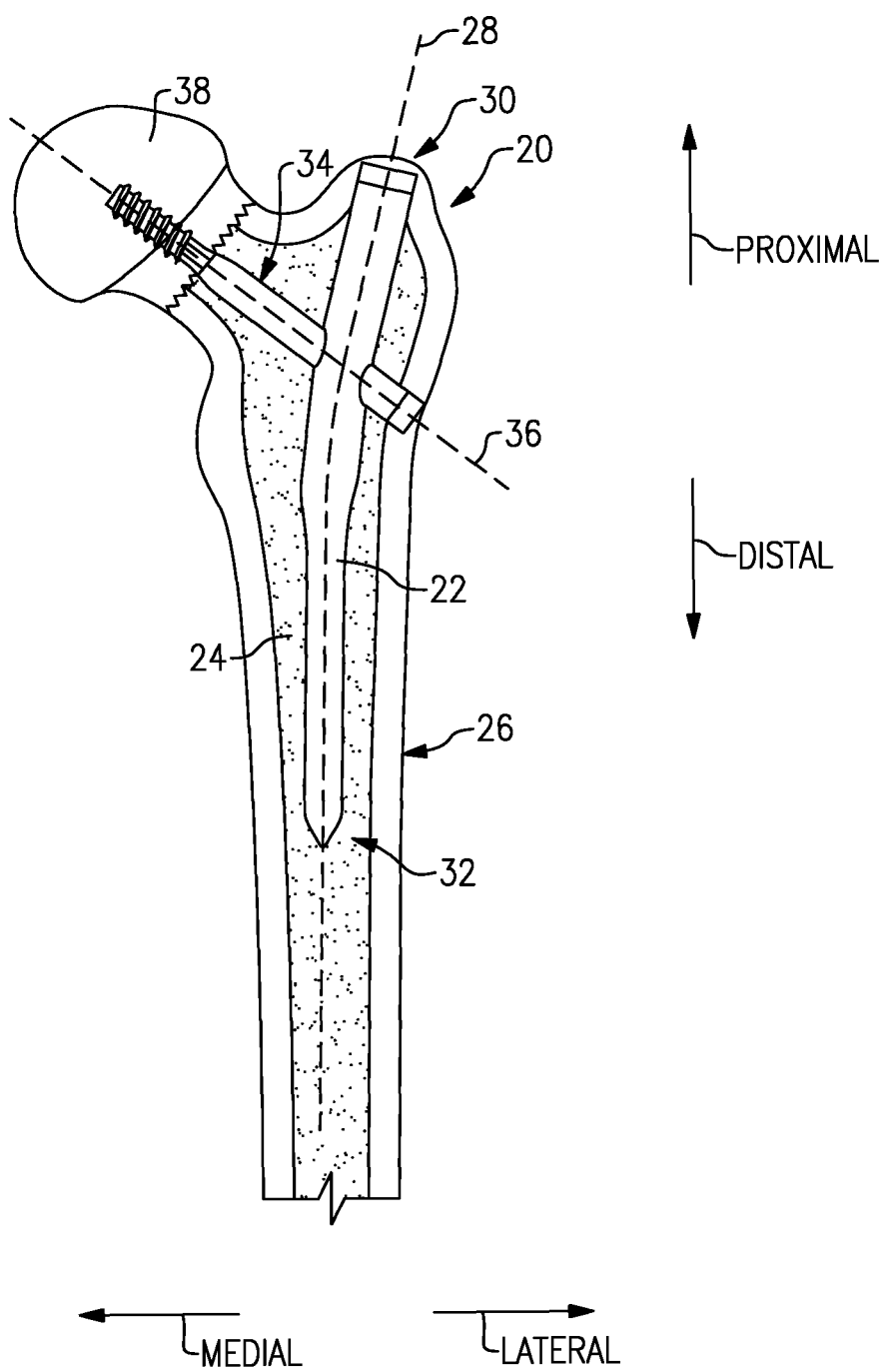
FIG. 1 illustrates an example bone fixation device relative to a fractured bone.

FIG. 1 illustrates an example bone fixation device 20. In this example, the bone fixation device 20 is an intramedullary nail. More specifically, the bone fixation device 20 is a proximal femoral nail. The bone fixation device 20 includes a nail 22 received within the medullary cavity 24 of a femur 26. The illustrated femur 26 is a left femur. The nail 22 extends along a longitudinal axis 28 from a proximal end 30 to a distal end 32. The "proximal" and "distal" directions are labeled in the figures. The nail 22 may be inserted into the medullary cavity 24 using known techniques, including making use of tools such as a cannulated reamer, guiding wire, and an aiming jig, among others.

The fixation device 20 further includes a screw assembly 34 received within a transverse bore (discussed below) in the nail 22. The screw assembly 34 extends along a transverse axis 36. The transverse axis 36 extends generally in the "lateral" and "medial" directions, and intersects the longitudinal axis 28. In this disclosure, "transverse" means the transverse axis 36 intersects the longitudinal axis 28.

In this example, the screw assembly 34 engages a fractured bone fragment 38, which in this example includes a femoral head, and supports the fractured bone fragment 38 relative to the remainder of the femur 26 to promote healing. While a femoral neck fracture is illustrated, this disclosure applies to other types of fractures including intertrochanteric fractures, subtrochanteric fractures, etc. Further, the fixation device 20 could be used with other bones, and is not limited to use with a femur.

FIG. 1A illustrates an example cannulated awl 33. The awl 33 includes a pointed distal end 35 and a handle 37 at a proximal end 39. A shaft 41 extends between the distal and proximal ends 35, 39. The awl 33 is fully cannulated so as to allow a guide wire to be inserted in the medullary cavity 24. The shaft 41 is curved along its length, in this example, to assist in maneuvering the awl 33 into the medullary cavity 24.

The awl 33 further includes a rasper 43 adjacent the distal end 35, which also assists in maneuvering the awl 33 within the medullary cavity 24. The rasper 43 is spaced-apart from the distal end 35 and includes a plurality of rows of staggered teeth 45. Further, the rasper 43 is tapered, and the outer dimension of the rasper 43 increases proximally.

In addition to the staggered teeth 45, the rasper 43 could include a plurality of longitudinal channels 47 (FIG. 1B) along its length to allow transportation of bone and/or bone marrow away from the distal end 35. Alternatively, in place of staggered teeth, the rasper 43 in some examples includes ribs 49 (FIG. 1C). When the rasper 43 includes ribs 49, the rasper 43 may also include channels 47 (FIG. 1D).

After a guide wire is fed into the medullary cavity 24 by way of the awl 33, a reamer 51 (FIG. 1E) follows the guide wire and is used to ream a passageway for the nail 22. Next, the nail 22 is connected to an aiming jig 53 (FIG. 1F), which is used to insert the nail 22 into the medullary cavity 24. In this example, the aiming jig 53 includes an adjustable nail-jig interface 55 (FIG. 1G).

With reference to FIG. 1G, the nail-jig interface 55 is provided by a screw 57 having a curved guide 59 configured to slide within a slot 61. The slot 61 includes a lateral end 63 and a medial end 65 (FIG. 1H), and is sized to accommodate several sizes and shapes of the nail 22. In FIG. 1H, for example, the nail 22 is sized such that, when the screw 57 engages the nail 22, the curved guide 59 abuts the lateral end 63 of the slot 61. FIG. 1I shows a different nail size, and in that example the curved guide 59 settles between the lateral and medial ends 63, 65. Finally, FIG. 1J shows yet another nail size, which causes the curved guide 59 to abut the medial end 65.

Again, the jig 53 is used to insert the nail 22 into the medullar cavity 24. Once inserted, the jig 53 is also used to align another reamer 67 along the transverse axis 36 (FIG. 1F). Once reamed, the aiming jig 53 is used to guide the screw assembly 34 along the transverse axis 36 and into the position of FIG. 1.

Figure 2:
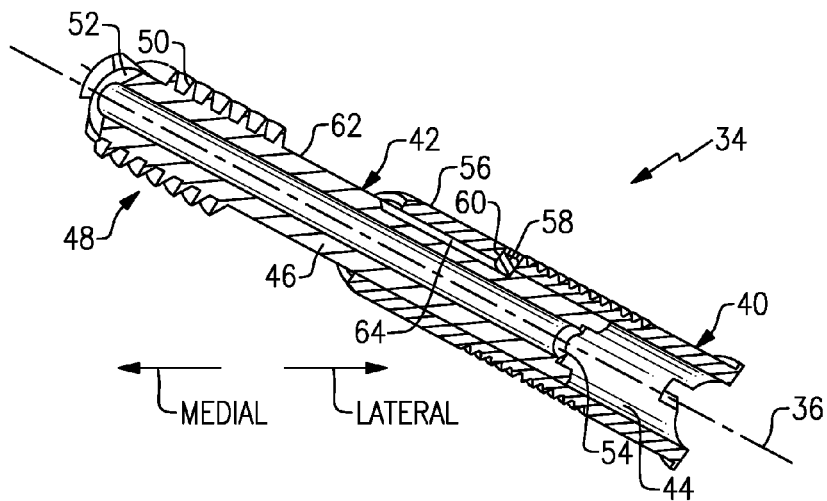
FIG. 2 is a cross-sectional view of a first example screw assembly.

FIG. 2 is a cross-sectional view of one example screw assembly 34. In this example, the screw assembly 34 includes a sleeve 40 and a screw 42 received within a bore 44 of the sleeve 40. In an alternate example, the screw assembly 34 could be provided by a single piece. The one-piece example may be particularly beneficial when performing surgery on children or persons with relatively small anatomical features.

The screw 42 is cannulated and includes a shank 46 and a tip 48. The shank 46 is sized to be received within the bore 44, and the tip 48 includes threads 50. At a medial end, the tip 48 includes a rounded nose 52. At a lateral end, the shank 46 includes a drive socket 54 configured to mate with a driver, which rotates the screw 42 and facilitates engagement of the threads 50 with the fractured bone fragment 38.

When the screw 42 is initially inserted into the fractured bone fragment 38, the screw 42 is allowed to rotate relative to transverse axis 36. Once the screw 42 has been appropriately positioned in the fractured bone fragment 38, the screw 42 is prevented from rotating about the transverse axis 36.

In the illustrated example, the exterior surface 56 of the sleeve 40 receives a pin 58 in a threaded opening 60. The pin 58 welded into the threaded opening in this example and is configured to project inwardly, toward the transverse axis 36. The exterior surface 62 of the shank 46 includes a channel 64 configured to receive the pin 58. In the illustrated example, the pin 58 has a rounded tip abutting the channel 64. It should be understood that the pin 58 could be cylindrical and have a flat end face. In that example, the channel 64 may be replaced by, or include, a flat surface to correspond to the contour of the end of the pin 58. Further, it should be understood that there may be multiple channels 64 provided circumferentially about the shank 46.

The channel 64 has a width substantially equal to a width of the pin 58 such that, when the pin 58 is received in the channel 64, the pin 58 prevents relative rotation between the screw 42 and the sleeve 40. The channel 64 has a length substantially greater than the diameter of the pin 58, which allows the screw 42 to move along the transverse axis 36 relative to the sleeve 40 until the pin 58 abuts an end of the channel 64.

While a pin 58 and a channel 64 are illustrated in FIG. 2, this disclosure is not limited to such an arrangement. For instance, in the example of FIG. 3, the exterior surface 62 of the shank 46 includes a radially outward projection 66 configured to abut a face 68 of the sleeve 40 projecting radially inwardly from a medial end of the sleeve 40. The projection 66 and face 68, however, could be provided adjacent a lateral end of the screw 42, as shown in FIG. 4. In another example, shown in FIG. 5, the sleeve 40 is arranged similarly to the FIG. 3 embodiment, but the screw 42 includes deflectable latches 74 configured to abut the face 68.

Figure 3:
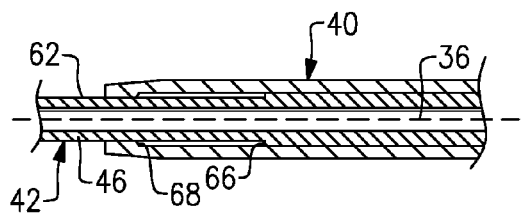
FIG. 3 is a cross-sectional view of a second example screw assembly.
Figure 4:
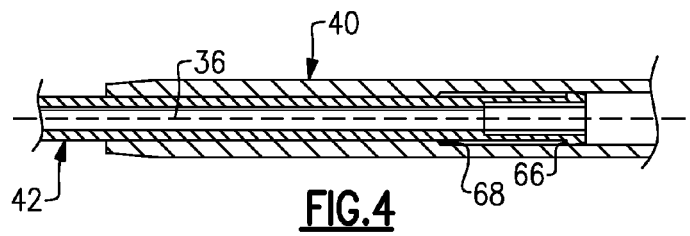
FIG. 4 is a cross-sectional view of a third example screw assembly.
Figure 5:
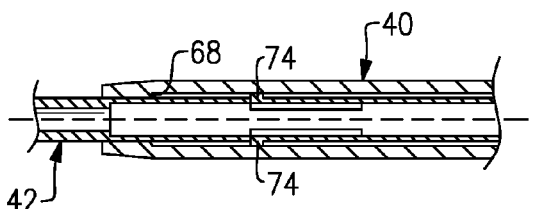
FIG. 5 is a cross-sectional view of a fourth example screw assembly.
Figure 6:
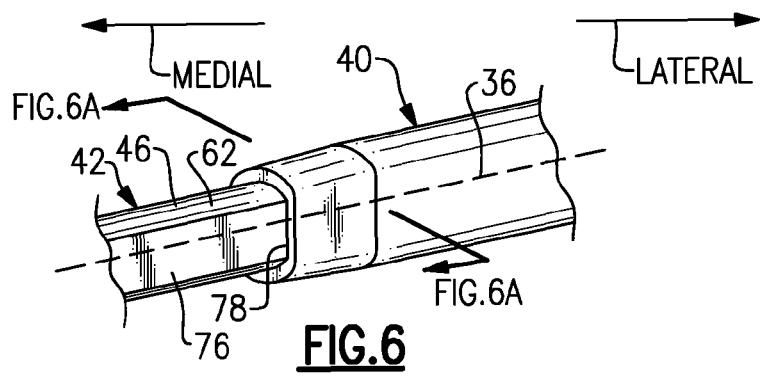
FIG. 6 is a perspective view illustrating an example engagement between a screw and a sleeve.

The embodiments of FIGS. 3-5 prevent axial movement of the screw 42 medially beyond a certain point, which in this example corresponds to the point where the projections 66 or latches 74 abut the face 68. In order to restrict relative rotation about the transverse axis 36, these embodiments can be arranged as shown in FIG. 6. In FIG. 6, the exterior surface 62 of the shank 46 includes a planar face 76 corresponding to a planar face 78 (FIG. 6A) of the interior of the sleeve 40. The planar faces 76, 78 extend in a direction substantially parallel to the transverse axis 36. This disclosure is not limited to the arrangements of FIGS. 3-6, and extends to other arrangements that restrict rotation and limit axial movement.

Figure 6A:
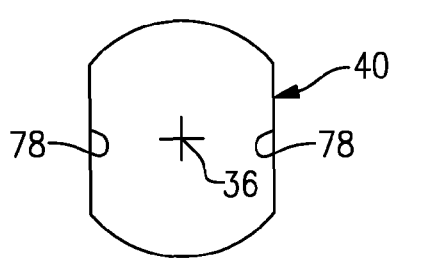
FIG. 6A is an illustration representative of a first example orientation of the interior of the sleeve.
Figure 6B:
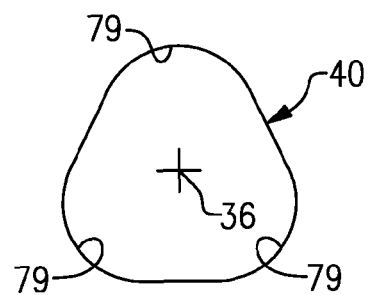
FIG. 6B is an illustration representative of a second example orientation of the interior of the sleeve.
Figure 6C:
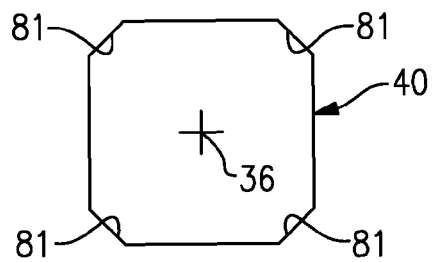
FIG. 6C is an illustration representative of a third example orientation of the interior of the sleeve.

While FIGS. 6 and 6A show one orientation that restricts rotation between the sleeve 40 and screw 42, FIGS. 6B and 6C illustrate other orientations. In FIG. 6B, the inner surface of the sleeve 40 resembles, in cross-section, a generally triangular shape with rounded corners 79. The exterior surface 62 of the shank 46 would be arranged similarly to correspond to the orientation of the sleeve 40. In FIG. 6C, the inner surface of the sleeve 40 resembles, in cross-section, a generally square shape with chamfered corners 81. While three orientations are illustrated, this disclosure extends to other orientations that restrict rotation while allowing axial movement.

Figure 7:
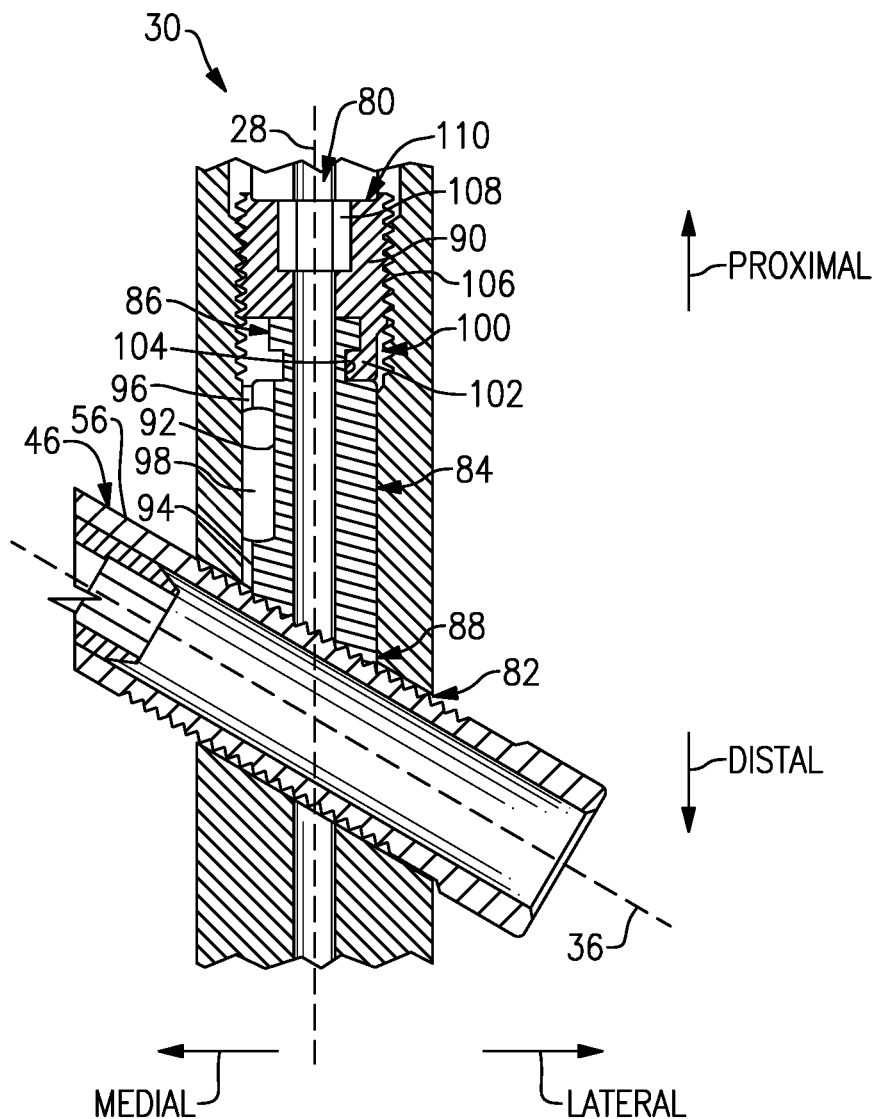
FIG. 7 is a cross-sectional view of the bone fixation device.

Once the screw 42 has been appropriately placed into the fractured bone fragment 38, the entire screw assembly 34 is then positioned and locked relative to the nail 22. With reference to FIG. 7, the nail 22 includes a longitudinal bore 80 extending along the longitudinal axis 28 from a proximal end 30 of the nail 22 to a transverse bore 82, which receives the screw assembly 34.

In this example, a locking device 84 is received in the longitudinal bore 80. The locking device 84 includes a proximal end 86 and a distal end 88. The proximal end 86 is connected to a set screw 90, and the distal end 88 is configured to engage the exterior surface 56 of the sleeve 40. The distal end 88 is curved and generally corresponds to the curvature of the exterior surface 56.

The locking device 84 is moveable along the longitudinal axis 28 without rotating. In this example, the locking device 84 includes a channel 92 (perhaps best seen in FIG. 9) provided in its exterior surface 94. The longitudinal bore 80 includes a channel 96 corresponding to the channel 92. An insert 98 is provided in the two channels 94, 96. The insert 98 is sized such that, when inserted in the two channels 94, 96, the locking device 84 does not rotate relative to the nail 22. The insert 98, however, does not prevent movement of the locking device 84 along the longitudinal axis 28.

A distal end 100 of the set screw 90 is provided with a tab 102, which is received in a corresponding recess 104 in the proximal end 86 of the locking device 84. The set screw 90 is threadably engaged at its exterior 106 with the longitudinal bore 80, and includes a drive socket 108 at is proximal end 110 configured to mate with a driver. Rotation of the set screw 90 results in movement of the locking device 84 along the longitudinal axis 28. The set screw 90 can be adjusted to an appropriate level, such that the locking device 84 imparts a sufficient level of force to the screw assembly 34.

The locking device 84 is configured to clasp the screw assembly 34, specifically the exterior surface 56 of the sleeve 40, and to lock the screw assembly 34 against movement along the transverse axis 36 and against rotation about the transverse axis 36. The locking device 84 of this disclosure thus eliminates the need for separate locking devices dedicated to preventing axial movement and rotation.

Figure 8:
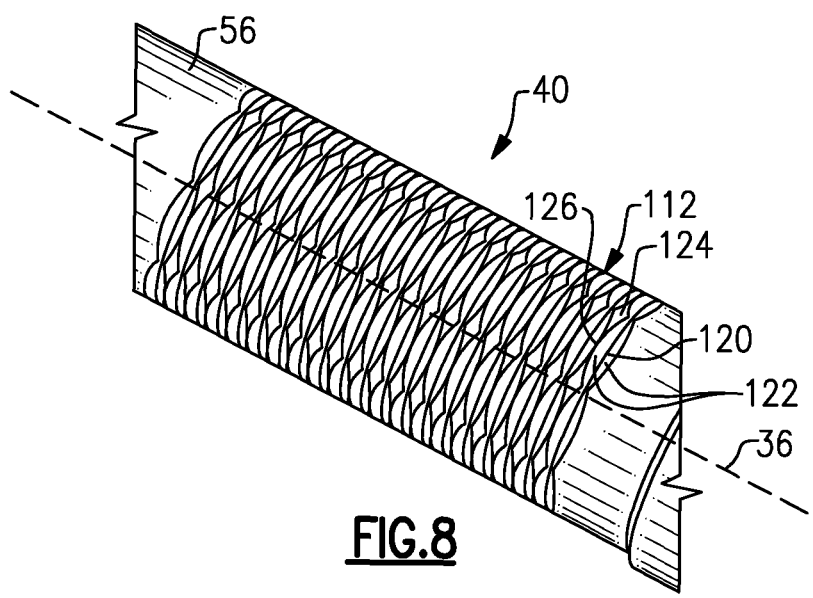
FIG. 8 is a close-up view of an exterior surface of the sleeve having an example wave-like knurled pattern.
Figure 9:
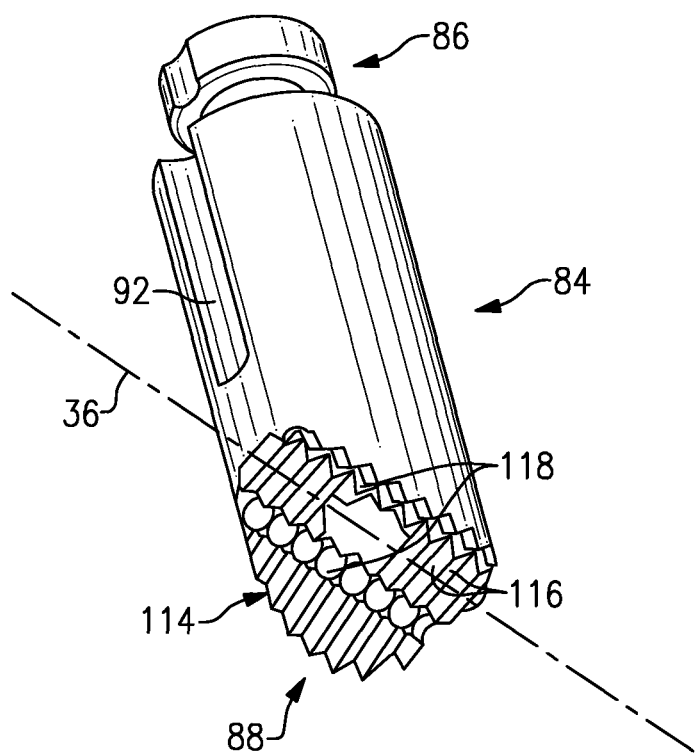
FIG. 9 is a close-up view of a distal surface of the locking device having a pattern corresponding to the pattern of FIG. 8.

With reference to FIGS. 8-9, the exterior surface 56 of the sleeve 40 is provided with a first pattern 112, and the distal end 88 of the locking device 84 is provided with a second pattern 114 configured to mate with the first pattern 112. In the example of FIGS. 8-9, the second pattern 114 includes a plurality of first faces 116 arranged substantially normal to the transverse axis 36 and a plurality of second faces 118 arranged substantially parallel to the transverse axis 36.

The first pattern 112 of the sleeve 40 in this example is provided by a knurled surface. In particular, this example includes a wave-like knurled surface. The wave-like knurled surface includes a plurality of depressions 120 formed between curved faces 122. When viewed from above, the curved faces 122 provide the depressions with a substantially elliptical shape. In particular, the shape is substantially a prolate spheroid, which is similar to the cross-sectional shape of an American football. Further, a plurality of smooth sections 124 are provided circumferentially between adjacent depressions 120. Near the midpoint of the projections, pointed peaks 126 are provided between adjacent curved faces 122.

The first faces 116 of the locking device 84 are configured to engage the faces 122 adjacent the pointed peaks 126, and the second faces 118 are configured to engage the faces 122 adjacent the smooth sections 124. In doing so, the contact between the first and second faces 116, 118 and the depressions 120 prevents axial movement of the sleeve 40 relative to the nail 22 along the transverse axis 36 and also prevents rotation of the sleeve 40 about the transverse axis 36.

Figure 10:
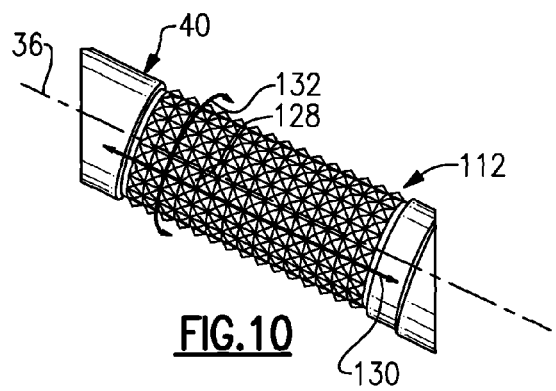
FIG. 10 is a close-up view of an exterior surface of the sleeve having an example diamond knurled pattern.
Figure 11:
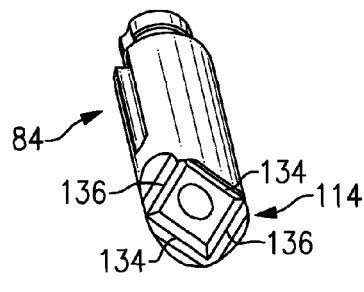
FIG. 11 is a close-up view of a distal surface of the locking device having a pattern corresponding to the pattern of FIG. 10.

While a wave-like knurled surface is illustrated in FIG. 8, the first and second patterns 112, 114 could be different patterns that restrict axial and rotational movement. In FIGS. 10-11, the first pattern 112 of the sleeve 40 is provided by a diamond knurled surface. In this example, a plurality of pyramid-shaped projections 128 are provided, and are arranged such that the first pattern provides a plurality of longitudinal and circumferential grooves 130, 132, respectively. The second pattern 114 of the locking device 84 includes a plurality of longitudinal projections 134 configured to engage the longitudinal grooves 130 and a plurality of circumferential projections 136 configured to engage the circumferential grooves 132. When engaged, the first and second patterns 112, 114 restrict both axial and rotational movement of the sleeve 40 relative to the nail 22.

Figure 12:
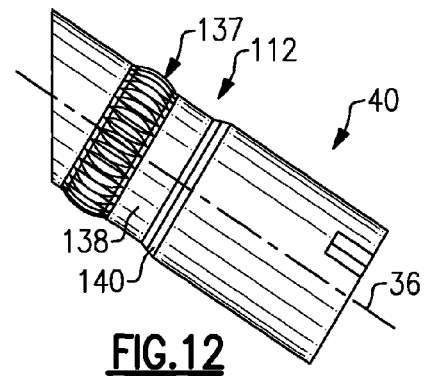
FIG. 12 is a close-up view of an exterior surface of the sleeve having yet another example pattern including splines and a smooth surface.
Figure 13:
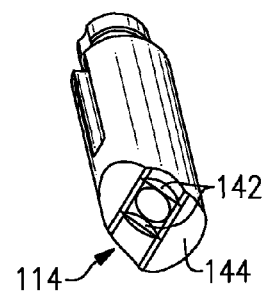
FIG. 13 is a close-up view of a distal surface of the locking device having a pattern corresponding to the pattern of FIG. 12.

FIGS. 12 and 13 show another embodiment. In this embodiment, the first pattern 112 includes a plurality of ellipse-shaped splines 137. The ellipse-shaped splines 137 are shaped similar to the depressions 120 of FIG. 8, but are oriented parallel to the transverse axis 36. The ellipse-shaped splines 137 are formed as a single ring extending circumferentially about the transverse axis 36. The sleeve 40 includes a smooth surface 138 lateral of the ellipse-shaped splines 137, and further includes a radially outward projection 140 lateral to the smooth surface 138. The splines 137 are configured to engage corresponding projections 142 provided in the second pattern 114, and a smooth surface 144 of the second pattern 114 is configured to abut the smooth surface 138 and be provided between the splines 137 and the radially outward projection 140 to restrict axial movement of the sleeve 40 relative to the nail 22.

Figure 14:
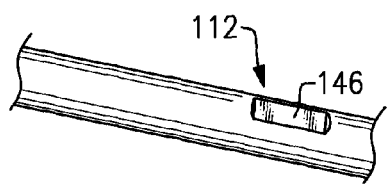
FIG. 14 is a close-up view of an exterior surface of the sleeve having an example pattern including a recessed flat.
Figure 15:
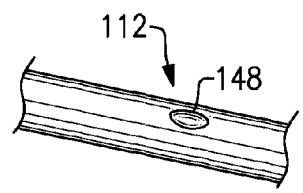
FIG. 15 is a close-up view of an exterior surface of the sleeve having an example pattern including a recessed elliptical-shape.

In other embodiments, the first pattern 112 could be provided by a recessed flat 146 (FIG. 14) or a recessed ellipse-shape 148 (FIG. 15). These patterns would mate with a locking device 84 provided with a corresponding second pattern 114 to restrict axial and rotational movement of the sleeve 40 relative to the nail 22. While several patterns 112, 114 have been discussed herein, this disclosure is not limited to any particular patterns. This disclosure extends to all patterns capable of restricting both axial and rotational movement.

Another aspect of this disclosure relates to reducing stress concentrations between the sleeve 40 and the nail 22 adjacent the transverse bore 82. In one example, illustrated in FIGS. 16-17, a lateral edge 150 of the transverse bore 82 is rounded with tangential transitions about its entire circumference. In other words, the lateral edge 150 is provided by a rounded surface 152 about its entire circumference without including any chamfered or flat sections. Further, the rounded surface 152 is smooth and uninterrupted about the transverse axis 36.

Figure 18:
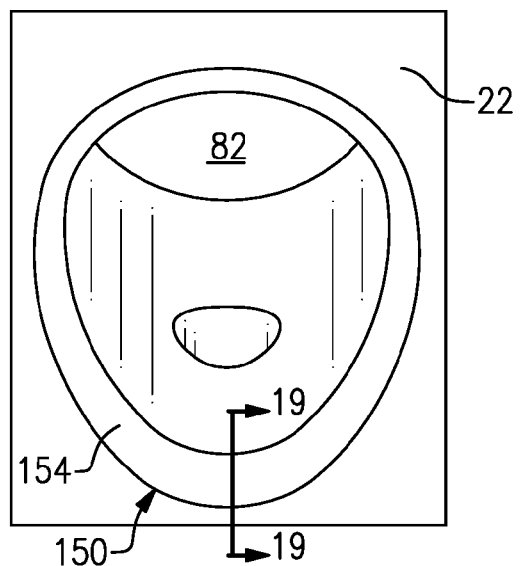
FIG. 18 illustrates a chamfered lateral edge of the transverse bore.
Figure 19:
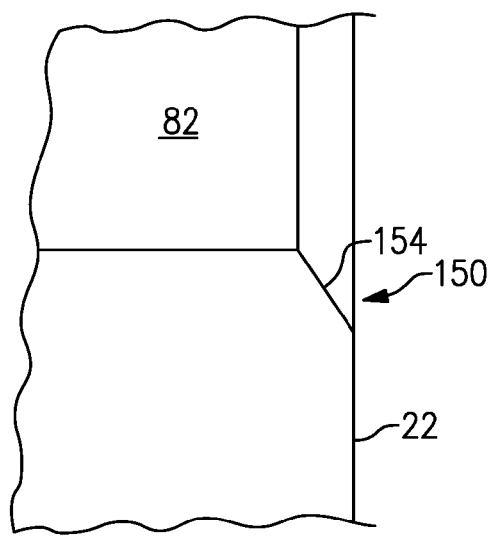
FIG. 19 is a view taken along line 19-19 and illustrates the chamfered lateral edge in detail.

In another example, illustrated in FIGS. 18-19, the lateral edge 150 is chamfered about its entire circumference. The lateral edge 150 in this example is provided by a planar, chamfered surface 154. The angle of the chamfered surface 154 may change about the circumference of the lateral edge 150, but the chamfered surface 154 is not interrupted by any flat or rounded sections.

Figure 20:
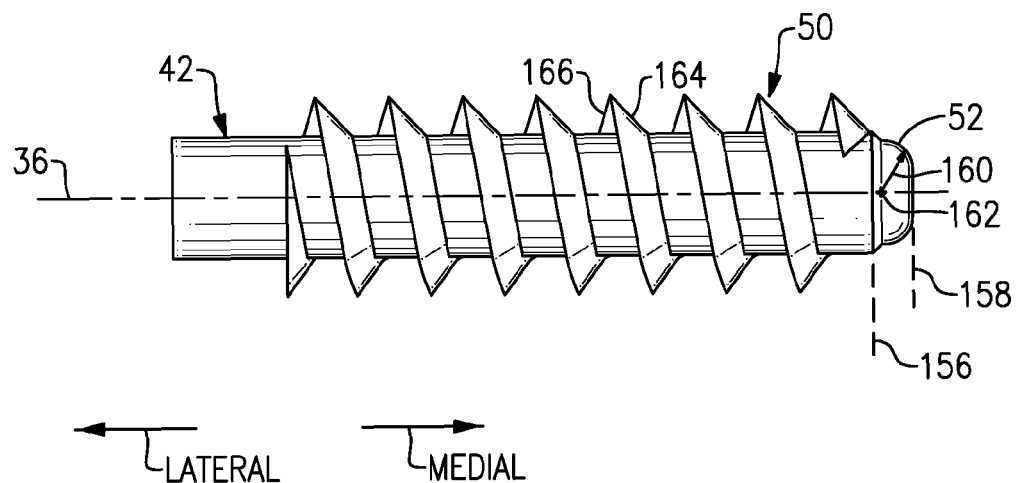
FIG. 20 illustrates a tip of the screw with standard threads.

With reference to FIG. 20, the rounded nose 52 of the screw 42 is rounded between a location 156 where the threads 50 end and the medial-most end 158 of the screw 42. In this example, the contour of the rounded nose 52 is provided by a constant radius 160 having an origin 162 spaced laterally from the medial-most end 158. The rounding of the nose 52 of the screw 42 increases the ease of transporting bone debris.

Figure 21:
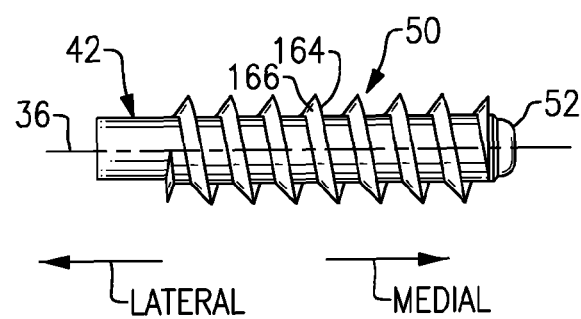
FIG. 21 illustrates a tip of the screw with reverse threads.

Further, in the example of FIG. 20, the threads 50 are standard threads. Specifically, the threads 50 have leading flanks 164 that are inclined in a lateral direction. The trailing flanks 166 project in a direction substantially normal to the transverse axis 36. In the example of FIG. 21, however, the screw includes reverse threads. In that case, the threads 50 have trailing flanks 166 that are inclined in a medial direction, and leading flanks 164 that project in a direction substantially normal to the transverse axis 36. While both types of threads can be used, reverse threads may have a benefit of an increased resistance to acetabular penetration.

It should be understood that terms such as "proximal," "distal," "medial," and "lateral" are used consistent with their art-accepted meanings, and are used for purposes of explanation only. Terms such as "longitudinal," "axial," "radial," and "circumferential" are used above with reference to the respective axis and are also used only for purposes of explanation, and should not be considered otherwise limiting. Terms such as "generally," "substantially," and "about" are not intended to be boundaryless terms, and should be interpreted consistent with the way one skilled in the art would interpret those terms.

Although the different examples have the specific components shown in the illustrations, embodiments of this disclosure are not limited to those particular combinations. It is possible to use some of the components or features from one of the examples in combination with features or components from another one of the examples.

One of ordinary skill in this art would understand that the above-described embodiments are exemplary and non-limiting. That is, modifications of this disclosure would come within the scope of the claims. Accordingly, the following claims should be studied to determine their true scope and content.

The invention claimed is:

1. A bone fixation device, comprising:
a nail extending along a longitudinal axis, the nail provided with a transverse bore arranged along a transverse axis that intersects the longitudinal axis;
a screw assembly received in the transverse bore; and
a locking device configured to clasp an exterior surface of the screw assembly to lock the screw assembly against movement along the transverse axis and against rotation about the transverse axis.

2. The bone fixation device as recited in claim 1, wherein:
the screw assembly includes a sleeve provided with a first pattern, and
a distal end of the locking device is provided with a second pattern configured to mate with the first pattern to lock the sleeve against movement along the transverse axis and against rotation about the transverse axis.

3. The bone fixation device as recited in claim 2, wherein the first and second patterns are provided by one of (1) a wave-like knurled surface, (2) a diamond knurled surface, (3) a plurality of splines, (4) a recessed flat, and (5) a recessed ellipse-shape.

4. The bone fixation device as recited in claim 1, wherein a lateral edge of the transverse bore is chamfered about its entire circumference.

5. The bone fixation device as recited in claim 1, wherein a lateral edge of the transverse bore is rounded with tangential transitions about its entire circumference.

6. The bone fixation device as recited in claim 1, wherein:
the screw assembly includes a sleeve and a screw,
the screw is received in a bore of the sleeve, and
the sleeve is configured to limit axial movement and restrict rotation of the screw about the transverse axis.

7. The bone fixation device as recited in claim 6, wherein the screw includes an exterior surface with a channel, and wherein a pin projects into the channel to restrict relative rotation of the screw about the transverse axis.

8. The bone fixation device as recited in claim 6, wherein the sleeve includes a face configured to abut an outward projection of the screw.

9. The bone fixation device as recited in claim 6, wherein the sleeve includes a face configured to abut a latch of the screw.

10. The bone fixation device as recited in claim 1, wherein the screw assembly includes a screw having a distal end with threads and a rounded nose.

11. The bone fixation device as recited in claim 10, wherein the distal end includes reverse threads.

12. The bone fixation device as recited in claim 1, wherein the bone fixation device is a proximal femoral nail.

13. The bone fixation device as recited in claim 2, wherein the first pattern includes a plurality of first faces arranged substantially normal to the transverse axis and a plurality of second faces arranged substantially parallel to the transverse axis.

14. The bone fixation device as recited in claim 13, wherein a plurality of depressions are defined between the first faces and the second faces, and wherein the depressions are shaped substantially as prolate spheroids.

15. The bone fixation device as recited in claim 1, wherein a distal end of the locking device is curved about the transverse axis.

16. A bone fixation device, comprising:
a nail extending along a longitudinal axis, the nail provided with a transverse bore arranged along a transverse axis that intersects the longitudinal axis;
a screw assembly received in the transverse bore; and
a locking device configured to clasp the screw assembly to lock the screw assembly against movement along the transverse axis and against rotation about the transverse axis, wherein the locking device is received in a bore in a proximal end of the nail, the locking device being moveable along the longitudinal axis of the nail without rotating.

17. The bone fixation device as recited in claim 16, wherein a set screw is received in the bore in the proximal end of the nail, and wherein rotation of the set screw results in movement of the locking device along the longitudinal axis of the nail.

18. A bone fixation device, comprising:
a nail extending along a longitudinal axis, the nail provided with a transverse bore arranged along a transverse axis that intersects the longitudinal axis;
a screw assembly received in the transverse bore, the screw assembly including a sleeve provided with a first pattern; and
a locking device configured to clasp an exterior surface of the screw assembly to lock the screw assembly against movement along the transverse axis and against rotation about the transverse axis, wherein a distal end of the locking device is provided with a second pattern configured to mate with the first pattern to lock the sleeve against movement along the transverse axis and against rotation about the transverse axis.

19. The bone fixation device as recited in claim 18, wherein the sleeve is configured to limit axial movement and restrict rotation of the screw about the transverse axis.

20. The bone fixation device as recited in claim 19, wherein the screw includes an exterior surface with a channel, and a pin projects into the channel.

21. The bone fixation device as recited in claim 18, wherein the first pattern includes a plurality of first faces arranged substantially normal to the transverse axis and a plurality of second faces arranged substantially parallel to the transverse axis.

22. A method of fixing fractured bone fragments relative to one another to promote healing, comprising:
   inserting a nail into a medullary cavity of a bone, the nail extending along a longitudinal axis and a transverse bore arranged along a transverse axis that intersects the longitudinal axis;
   engaging a fractured fragment of the bone with a screw received through the transverse bore;
   positioning a sleeve provided outside the screw within the transverse bore, the sleeve configured to limit movement of the screw along the transverse axis, and to prevent rotation of the screw about the transverse axis; and
   clasping an exterior surface of the sleeve with a locking device, the locking device configured to prevent movement of the sleeve along the transverse axis, and to prevent rotation of the sleeve about the transverse axis.

23. The method as recited in claim 22, further comprising:
   a pin projecting into a channel formed in an exterior surface of the screw, the pin limiting the axial movement of the screw relative to the transverse axis and preventing rotation of the screw about the transverse axis.

24. The method as recited in claim 22, wherein the step of positioning the sleeve includes positioning a femoral head to promote healing of the fractured fragment.

25. The method as recited in claim 22, wherein the sleeve includes a plurality of first faces arranged substantially normal to the transverse axis and a plurality of second faces arranged substantially parallel to the transverse axis, and wherein the locking device is configured to mate with the first and second faces.

\* \* \* \* \*